(12) United States Patent
Alshatwi et al.

(10) Patent No.: US 10,451,557 B2
(45) Date of Patent: Oct. 22, 2019

(54) PH SENSING BIOFILM

(71) Applicant: KING SAUD UNIVERSITY, Riyadh (SA)

(72) Inventors: Ali Abdullah Alshatwi, Riyadh (SA); Jegan Athinarayanan, Riyadh (SA); Periasamy Vaiyapuri Subbarayan, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 15/962,915

(22) Filed: Apr. 25, 2018

(65) Prior Publication Data
US 2019/0128815 A1 May 2, 2019

Related U.S. Application Data

(62) Division of application No. 15/802,055, filed on Nov. 2, 2017, now Pat. No. 10,054,548.

(51) Int. Cl.
*G01N 21/80* (2006.01)
*G01N 33/02* (2006.01)
*G01N 21/77* (2006.01)

(52) U.S. Cl.
CPC ............. *G01N 21/80* (2013.01); *G01N 33/02* (2013.01); *G01N 2021/7796* (2013.01)

(58) Field of Classification Search
CPC ........ G01N 21/80; G01N 21/78; G01N 21/77; G01N 21/75; G01N 33/02; G01N 2021/7796
USPC ....................................................... 436/163
See application file for complete search history.

(56) References Cited

U.S. PATENT DOCUMENTS

| 7,807,877 B2 | 10/2010 | Brugliera |
| 2009/0197973 A1 | 8/2009 | Arakawa |
| 2013/0017239 A1 | 1/2013 | Viladot Petit |
| 2013/0216596 A1 | 8/2013 | Viladot Petit |
| 2016/0002483 A1* | 1/2016 | Zhao ........................ A23B 7/16 426/102 |

FOREIGN PATENT DOCUMENTS

| CN | 101788496 A | 7/2010 |
| DE | 2459226 A1 | 6/1976 |
| JP | 10282002 A | 10/1998 |
| KR | 20090087296 A | 8/2009 |

OTHER PUBLICATIONS

Pereira Jr., et al., "Active chitosan/PVA films with anthocyanins from *Brassica oleraceae* (Red Cabbage) as Time-Temperature Indicators for application in intelligent food packaging," Food Hydrocolloids, 43 Jan. 2015, 180-188.
Shukla, et al., "Development of on package indicator sensor for real-time monitoring of meat quality," Veterinary World, 8(3): 393-397, Mar. 2015.
Vartiainen, J., et al., "Biopolymer Films and Coatings in Packaging Applications—A review of Recent Developments," Materials Sciences and Applications, (5): 708-718, 2014.
Othman, S.H., "Bio-nanocomposite Materials for Food Packaging Applications: Types of Biopolymer and Nano-sized Filler," (2): 296-303, 2014.
Technical Association of the Pulp and Paper Industry, "Acid-Insoluble Lignin in Wood and Pulp (Reaffirmation of T222 om-02)," TAPPI Press, Atlanta, 2006.
Samad, M. A. et al., "Antibacterial Properties and Effects of Fruit Chilling and Extract Storage on Antioxidant Activity, Total Phenolic and Anthocyanin Content of Four Date Palm (*Phoenix dactylifera*) Cultivars," Molecules (21)419: 1-14, 2016.
Devaraya, K. et al., "Reversible and Universal pH Sensing Cellulose Nanofibers for Health Monitor," Sensors and Actuators B, (21): 281-286, 2015.
Ma, Qianrun et al., "Preparation of a visual pH-sensing film based on tara gum incorporating cellulose and extracts from graph skins," Sensors and Actuators, (235): 401-407 (2016).
Pourjavaher, Simin et al., "Development of a colorimetric pH indicator based on bacterial cellulose nanofibers and red cabbage (*Brassica oleraceae*) extract," Carbohydrate Polymers, (156): 193-201, 2017.

* cited by examiner

*Primary Examiner* — Christine T Mui
(74) *Attorney, Agent, or Firm* — Richard C. Litman

(57) ABSTRACT

The pH sensing biofilms include anthocyanin and a cellulose nanostructure or a cellulose nanocomposite. The cellulose nanostructure can include cellulose nanofibrils. The cellulose nanocomposite can include a composite of cellulose nanofibrils and pectin or a composite of cellulose nanofibrils and alginate. The presence of the anthocyanin in the biofilm allows the biofilm to change color in response to pH changes, thereby allowing the biofilm to be used as an active visual indicator of decay.

12 Claims, 2 Drawing Sheets

PH SENSING BIOFILM

CROSS REFERENCE TO RELATED APPLICATIONS

This application is a divisional of U.S. Ser. No. 15/802,055, filed on Nov. 2, 2017, currently pending.

BACKGROUND

1. Field

The disclosure of the present patent application relates to material science, and particularly to pH sensing biofilms and to methods of making and using pH sensing biofilms.

2. Description of the Related Art

Conventional food packaging materials provide four key functions: communication, protection, convenience, and containment. These packaging materials are designed to reduce food loss by extending shelf life. However, conventional food packaging materials cannot monitor the quality or safety of food products in real time. Conventional food packaging materials are also often manufactured from plastics which are not environmentally friendly either in production or disposal.

Recent developments in food packaging have included the application of nanostructured materials to improve mechanical strength and provide functional properties, such as antioxidant, antimicrobial, and food deterioration monitoring activities. Food deterioration monitoring has been proposed by numerous active means, such as, measuring volatile organic gases, use of pH indicators, use of nucleophilic sensing dyes, and detection of lactic acid levels. However, the field is still searching for a low cost, biodegradable, effective intelligent food packaging material.

Thus, pH sensing biofilms solving the aforementioned problems are desired.

SUMMARY

The pH sensing biofilms include anthocyanin and a cellulose nanostructure or anthocyanin and a cellulose nanocomposite. The cellulose nanostructure can include cellulose nanofibrils. The cellulose nanocomposite can include a composite of cellulose nanofibrils and pectin or a composite of cellulose nanofibrils and alginate. The presence of the anthocyanin in the biofilm allows the biofilm to change color in response to pH changes, thereby allowing the biofilm to be used as an active visual indicator of decay. The pH sensing biofilm is environmentally friendly and biodegradable. The pH sensing biofilm can be used in food packaging systems for detecting food decay.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

A pH sensing biofilm includes anthocyanin and a cellulose nanostructure or anthocyanin and a cellulose nanocomposite. The anthocyanin can be impregnated within the cellulose nanostructure or cellulose nanocomposite. The cellulose nanostructure can include cellulose nanofibrils (CNF). The cellulose nanocomposite can include a composite of cellulose nanofibrils and pectin (CNF-Pectin) or a composite of cellulose nanofibrils and alginate (CNF-alginate). When the biofilm is contacted with a surface, the biofilm can change color to indicate a pH change of the surface. For example, the biofilm can be affixed to meat or other food products to serve as an active visual indicator of decay. Accordingly, the pH sensing biofilm can be part of an environmentally friendly, biodegradable food packaging system.

The anthocyanin may be extracted from *Petunia hybrida*. The *Petunia hybrida* may be collected from Riyadh, Saudi Arabia. The CNF may be extracted from *Phoenix dactylifera*. The *Phoenix dactylifera* may be collected from Riyadh, Saudi Arabia.

Figure 1:
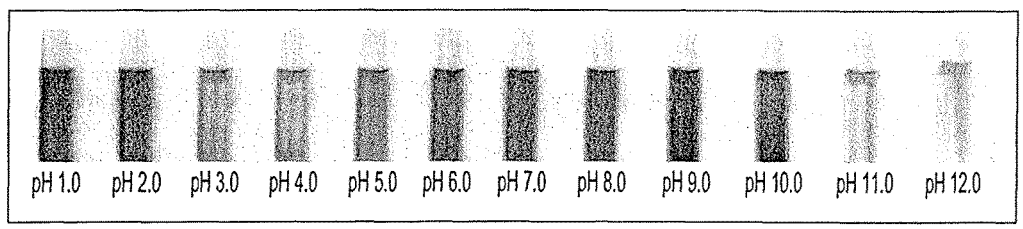
FIG. 1 is a picture of the color response of anthocyanin extracted from *Petunia hybrida* to a wide range of pH values.
Figure 2:
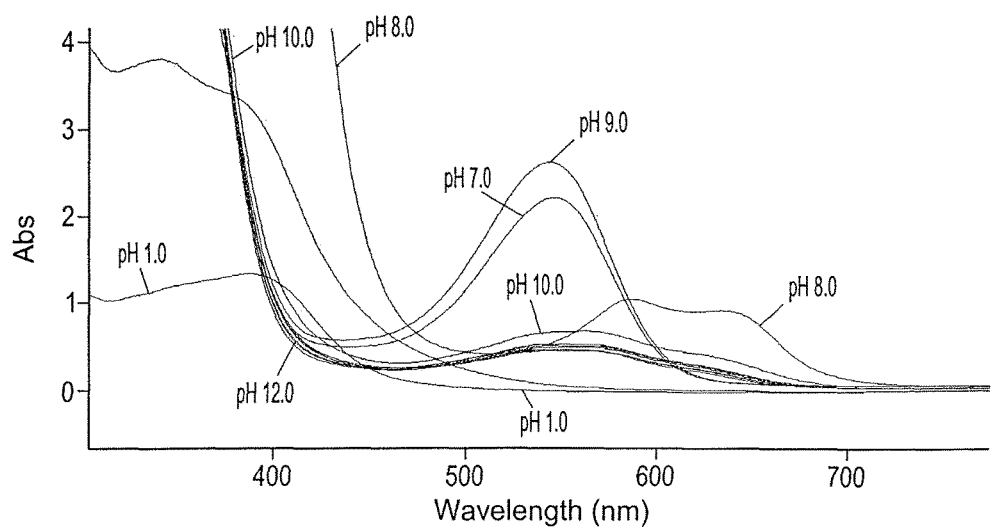
FIG. 2 is a graph of the UV-spectra of the anthocyanin extracted from *Petunia hybrida* exposed to a range of pH values.

The present inventors have found that the extracted *Petunia hybrida* anthocyanin may change color based upon pH and that the color change is visible to the naked eye. Further, when the anthocyanin was tested with different solutions having varying pH, it was found that a specific anthocyanin color can be associated with a specific pH. The various anthocyanin colors observed and the respective associated pH are provided in FIG. 1 and include: pH 1=rose, pH 2=Pink, pH 3=pale pink, pH 4=Silver, pH 5=Lavender, pH 6=Dark Lavender, pH 7=Lilac, pH 8=violet, pH 9=Indigo, pH 10=Green, pH 11=Yellow, and pH 12=Dark Yellow. These pH dependent color changes are further characterized by the ultra-violet visible spectra of FIG. 2. FIG. 2 depicts the UV-Vis spectra of the *Petunia hybrida* anthocyanin at different pH levels (ranging from pH 1.0 to pH 12). FIG. 2 shows that the absorbance of *Petunia hybrida* extracted anthocyanin differs based upon pH.

Figure 3:
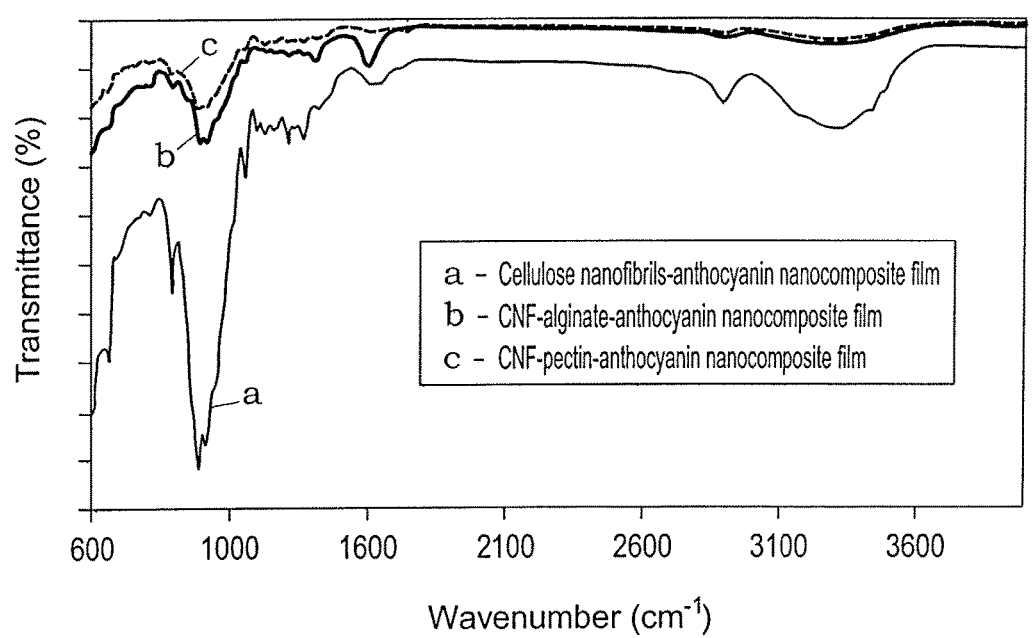
FIG. 3 is the Fourier transform infrared spectroscopy spectra of (a) cellulose nanofibrils labelled with anthocyanin, (b) CNF-alginate nanocomposite labelled with anthocyanin, and (c) CNF-pectin nanocomposite labelled with anthocyanin.

FIG. 3 illustrates the FT-IR spectra of the biofilm including anthocyanin and a cellulose nanostructure, e.g., CNF, or cellulose nanocomposite, CNF-alginate, or CNF-pectin. The FT-IR spectrum of the CNF-anthocyanin shows peaks at 671, 717, 852, 938, 997, 1162, 1360, 1380, 1478, 1662, and 2918 cm$^{-1}$. The spectra of CNF-alginate-anthocyanin and CNF-pectin-anthocyanin contained peaks corresponding to the CNF-anthocyanin spectra, confirming polymer nanocomposite formation.

The following examples illustrate the present teachings.

Example 1

Extraction of Anthocyanin from *Petunia hybrida*

*Petunia hybrida* flowers were collected from the campus of King Saud University, in Riyadh, Saudi Arabia. Ten grams of fresh purple *Petunia hybrida* flowers were immersed in a mixture of methanol and water at a ratio of about 70:30. The resulting mixture was blended and then sonicated at 750 W for about 15 minutes using a 20 kHz sonicator and a 13 mm diameter ultrasound probe tip. The resulting product was filtered using any conventional filter paper and stored in a dark location at about 4° C. The resulting anthocyanin solution was observed to be dark purple in color.

Example 2

Extraction of CNF from *Phoenix dactylifera*

*Phoenix dactylifera* biomass was collected from the campus of King Saud University in Riyadh, Saudi Arabia. The biomass was dried and pulverized. Twenty five grams of biomass was mixed with about 6% sodium hydroxide in a hydrothermal reactor kept at about 140° C. for about 2 hours. The alkali-exposed biomass was then washed with tap water until the pH was neutralized. The residue was then bleached with about 1.5% sodium hypochlorite solution. A resulting white material was mixed with about 40% sulfuric acid and kept at about 40° C. for about 35 minutes. Subsequently, the solution was transferred to a deep freezer at about −86° C. for an hour. The acid residues were washed from the material using centrifugation and the resulting pellet was sonicated at about 750 W for about 10 minutes using a 20 kHz sonicator. The resulting prepared CNF was characterized using X-ray diffraction (XRD) and transmission electron microscopy (TEM). The CNF XRD pattern exhibited cellulose I structure associated with (101), (021), (002), and (004) planes. TEM images confirmed that the CNF had a diameter between about 20-45 nanometers and were about 2-3 micrometers long. The CNF were observed to be organized in a netting arrangement with a fibrillated structure.

Example 3

Preparation of pH Sensing Biofilms

CNF nanocomposites were prepared by adding CNF prepared according to Example 2 to pectin or alginate at ratios of about 1:1, 1:2, and 1:3. Prepared CNF, CNF-Pectin, and CNF-Alginate were mixed with anthocyanin extracted from *Petunia hybrida* according to Example 1. About 1 g CNF or CNF-Pectin or CNF-Alginate was mixed with about 10 ml anthocyanin extract and about 100 ml of distilled water. These mixtures were sonicated for 20 minutes, poured into petri dishes, and kept in an oven at about 75° C. for about 24 hours.

The surface morphology of the pH sensing biofilms was observed at different magnifications and exhibited an organized structure. The pH sensing biofilms were immersed in pH solutions ranging from pH 1.0 to pH 12.0 for about 10 minutes. The films exhibited color change based upon the pH of the solution as follows: pH 1=Rose, pH 2=Pink, pH 3=Pale Pink, pH 4=Silver, pH 5=Lavender, pH 6=Dark Lavender, pH 7=Lilac, pH 8=Violet, pH 9=Indigo, pH 10=Green, pH 11=Yellow, pH 12=Dark Yellow.

Example 4

Meat Deterioration Sensing by pH Sensing BioFilms

Biofilms prepared according to Example 3 were fixed on about 50 grams of fresh chicken breast and these samples were stored at room temperature. Over time, the color of the film changed from Lavender to Violet, indicating an increased pH resulting from the deterioration of the chicken meat.

It is to be understood that the pH sensing biofilms are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of manufacturing a pH sensing biofilm, comprising:
   extracting anthocyanin from *Petunia hybrida*;
   extracting cellulose nanofibrils from *Phoenix dactylifera*;
   mixing the cellulose nanofibrils with the anthocyanin to provide a mixture;
   sonicating the mixture to provide a sonicated mixture; and
   drying the sonicated mixture.

2. The method of claim 1 further comprising harvesting the *Phoenix dactylifera* in Riyadh, Saudi Arabia.

3. The method of claim 1 further comprising harvesting the *Petunia hybrida* in Riyadh, Saudi Arabia.

4. The method of claim 1, wherein extracting the anthocyanin comprises extracting anthocyanin from *Petunia hybrida* petals.

5. The method of claim 4, wherein the extracting comprises:
   immersing the *Petunia hybrida* petals in a mixture of methanol and water at a 70:30 ratio to provide a second mixture;
   blending the second mixture;
   sonicating the mixture after blending to provide a sonicated mixture; and
   filtering the sonicated mixture to obtain anthocyanin extract.

6. The method of claim 1, wherein extracting the cellulose nanofibrils comprises extracting cellulose nanofibrils from dried *Phoenix dactylifera* biomass.

7. The method of claim 6, wherein extracting cellulose nanofibrils from dried *Phoenix dactylifera* biomass comprises:
   mixing the dried *Phoenix dactylifera* biomass with sodium hydroxide in a hydrothermal reactor to provide an alkaline mixture;
   washing the alkaline mixture with water to provide a pH neutralized product;
   adding sodium hypochlorate solution to the pH neutralized product to provide a bleached product;
   mixing the bleached product with sulfuric acid to provide a solution;
   maintaining the solution at about −86° C. for about an hour to provide a precipitate;
   washing the precipitate using centrifugation to provide a pellet; and
   sonicating the pellet to provide the cellulose nanofibrils.

8. A method of manufacturing a pH sensing biofilm, comprising:
   extracting anthocyanin from *Petunia hybrida*;
   extracting cellulose nanofibrils from *Phoenix dactylifera*;
   preparing a nanocomposite including the cellulose nanofibrils;
   mixing the nanocomposite with the anthocyanin to provide a mixture; and
   sonicating the mixture to provide a sonicated mixture; and
   drying the sonicated mixture.

9. The method of claim 8, wherein preparing the nanocomposite comprises:
mixing the cellulose nanofibrils with pectin at a ratio selected from the group consisting of a 1:1 ratio, a 1:2 ratio, and a 1:3 ratio.

10. The method of claim 8, wherein preparing the nanocomposite comprises:
mixing the cellulose nanofibrils with alginate at a ratio selected from the group consisting of a 1:1 ratio, a 1:2 ratio, and a 1:3 ratio.

11. The method of claim 8, wherein extracting the anthocyanin comprises:
immersing *Petunia hybrida* petals in a mixture of methanol and water at a 70:30 ratio to provide a second mixture;
blending the second mixture;
sonicating the second mixture after blending to provide a sonicated mixture; and
filtering the sonicated mixture to obtain anthocyanin extract.

12. The method of claim 8, wherein extracting cellulose nanofibrils comprises:
mixing dried *Phoenix dactylifera* biomass with sodium hydroxide in a hydrothermal reactor to provide an alkaline mixture;
washing the alkaline mixture with water to provide a pH neutralized product;
adding sodium hypochlorate solution to the pH neutralized product to provide a bleached product;
mixing the bleached product with sulfuric acid to provide a solution;
maintaining the solution at about −86° C. for about an hour to provide a precipitate;
washing the precipitate using centrifugation to provide a pellet; and
sonicating the pellet to provide the cellulose nanofibrils.

\* \* \* \* \*